(12) United States Patent
Beitle et al.

(10) Patent No.: US 11,052,330 B2
(45) Date of Patent: Jul. 6, 2021

(54) SIMPLE LAMP PCR DESIGN FOR LOW RESOURCE SETTING AND MINIMAL ENVIRONMENTAL FOOTPRINT

(71) Applicants: BOARD OF TRUSTEES OF THE UNIVERSITY OF ARKANSAS, Little Rock, AR (US); NowDiagnostics, Springdale, AR (US)

(72) Inventors: Robert Beitle, Fayetteville, AR (US); Christa N. Hestekin, Fayetteville, AR (US); Ahmed Elmasheiti, Fayetteville, AR (US); Kimberly Cribbs, Pea Ridge, AR (US); Michael Rienisch, Fayetteville, AR (US); Bryce Cameron Jones, Flower Mound, TX (US); Allysa Swearingen, Farmington, AR (US); Brandon Hart, Fort Smith, AR (US); Kevin Clark, Springdale, AR (US); Vicki Thompson, Springdale, AR (US)

(73) Assignees: Board Of Trustees Of The University Of Arkansas, Little Rock, AR (US); NowDiagnostics, Inc., Springdale, AR (US)

( * ) Notice: Subject to any disclaimer, the term of this patent is extended or adjusted under 35 U.S.C. 154(b) by 623 days.

(21) Appl. No.: 15/476,753

(22) Filed: Mar. 31, 2017

(65) Prior Publication Data
US 2017/0283858 A1 Oct. 5, 2017

Related U.S. Application Data

(60) Provisional application No. 62/316,345, filed on Mar. 31, 2016.

(51) Int. Cl.
| | | |
|---|---|---|
| *C12Q 1/68* | (2018.01) |
| *B01D 21/26* | (2006.01) |
| *C12Q 1/6806* | (2018.01) |
| *C12N 15/10* | (2006.01) |
| *G01N 1/30* | (2006.01) |
| *B01L 7/00* | (2006.01) |
| *B01L 9/06* | (2006.01) |
| *C12Q 1/6844* | (2018.01) |
| *G01N 31/22* | (2006.01) |

(52) U.S. Cl.
CPC ........... *B01D 21/262* (2013.01); *B01D 21/26* (2013.01); *B01L 7/00* (2013.01); *B01L 9/06* (2013.01); *C12N 15/1006* (2013.01); *C12Q 1/6806* (2013.01); *C12Q 1/6844* (2013.01); *G01N 1/30* (2013.01); *B01L 2200/10* (2013.01); *B01L 2200/147* (2013.01); *B01L 2300/0627* (2013.01); *B01L 2300/18* (2013.01); *B01L 2300/1877* (2013.01); *G01N 31/22* (2013.01); *G01N 2001/302* (2013.01)

(58) Field of Classification Search
None
See application file for complete search history.

(56) References Cited

U.S. PATENT DOCUMENTS

| | | | | |
|---|---|---|---|---|
| 5,721,123 A | * | 2/1998 | Hayes | B01L 7/52 |
| | | | | 435/6.11 |
| 2011/0312036 A1 | * | 12/2011 | Kojima | C12Q 1/6848 |
| | | | | 435/91.2 |

OTHER PUBLICATIONS

Kim et al. (Proc SPIE 6112, Microfluidics, BioMEMS, and Medical Microsystems IV, 611204 (Jan. 23, 2006) (Year: 2006).*
Ahmad et al. (Analytica Chimica Acta, 2012, p. 1-15) (Year: 2012).*
Hoehl et al. (Biomed Microdevices, 2014, 16:375-385) (Year: 2014).*
Mauk et al. (Mobile Health Technologies: Methods and Protocols, Methods in Molecular Biology, 2015, vol. 1256, p. Chapter 2, p. 1-40) (Year: 2015).*
Kim et al. (Lab Chip, 2009, 9(4):606-612) (Year: 2009).*
Sayad et al. (Sensors and Actuators B 227, 2016, 600-609) (Year: 2016).*
Notomi H, et al.; Loop-mediated isothermal amplification of DNA; Nucleic Acids Research (2000); vol. 28, No. 12, e63; Oxford University Press.
Parida M, et al.; Loop mediated isothermal amplification (LAMP): a new generation of innovative gene amplification technique; pserspectives in clinical diagnosis of infectious diseases; Review of Medical Virology (Aug. 20, 2008) Published online in Wiley InterScience doi: 10.1002/rmv.593.
Mori Y, et al.; Sequence specific visual detection of LAMP reactions by addition of cationic polymers; BMC Biotechnology (2006) 6, 3; http://www.biomedcentral.com/1472-6750/6/3.
Hodo H. et al; Purification Using Polyethylenimine Precipitation and low Molecular Weight Subunit Analysis of Calf Thymus and Wheat Germ DNA-Dependent RNA Polymerase II; Biochemistry (1977) 16, 2334.
Harwkins K, et al.; A Simple, Inexpensive Device for Nucleic Acid Amplification without Electricity—Toward Instrument—Free Molecular Diagnostics in Low-Resource Settings; PLOS (2011) doi 10.1371/journal.pone.0019738.
Weigl B, et al; Simplicity of use: a critical feature for widespread adoption of diagnostic technololgies in low-resource settings; Expert Rev Medical Devices (2009) 6, 461-464.

(Continued)

*Primary Examiner* — Stephanie K Mummert
(74) *Attorney, Agent, or Firm* — Keith A Vogt; Keith A. Vogt Ltd.

(57) ABSTRACT

The present invention provides a device and method for testing a material for the presence of DNA. The system includes a centrifuge, a microchip performing cell lysis and an enclosure that contains an isothermal ballast material and chromogenic agent that melts at a specific temperature and displays a color change, respectively.

20 Claims, 3 Drawing Sheets

(56) References Cited

OTHER PUBLICATIONS

Li et al; Sensitive and Rapid Detection of Giardia Iamblia Infection in Pet Dogs using Loop-Mediated Isothermal Amplification; Apr. 2013; National Center for Biotechnology Information; ; http://www.ncbi.nlm.nih.gov/pmc/articles/PMC3662070.

Kotloff K, et al; Global burden of Shigella infections: implications for vaccine development and implementation of control strategies; Bulletin of the World Health Organization (1999) 77, 651.

* cited by examiner

PROCESS OVERVIEW

BICYCLE CENTRIFUGE

DNA EXTRACTION: ADSORPTION TO SILICA

SIMPLE LAMP PCR DESIGN FOR LOW RESOURCE SETTING AND MINIMAL ENVIRONMENTAL FOOTPRINT

RELATED APPLICATIONS

This application claims the benefit of U. S. Provisional Application No. 62/316,345, filed Mar. 31, 2016, and herein incorporated by reference.

STATEMENT REGARDING FEDERALLY SPONSORED RESEARCH & DEVELOPMENT

Not applicable.

INCORPORATION BY REFERENCE OF MATERIAL SUBMITTED ON A COMPACT DISC

Not applicable.

BACKGROUND OF THE INVENTION

PCR (polymerase chain reaction) has been touted as a method of detection for numerous biologicals by virtue of the presence of DNA. Traditional PCR requires equipment that cycles temperature. Loop-mediated isothermal amplification polymerase chain reaction (LAMP PCR) is a recent development that requires a single temperature, but virtually all examples of its use still require some circuitry to monitor temperature and maintain it.

BRIEF SUMMARY OF THE INVENTION

In one embodiment, the present invention takes advantage of two materials, namely (1) an isothermal ballast material and (2) chromogenic agent that melts at a specific temperature and displays a color change, respectively. This embodiment represents an improvement in a LAMP PCR device that eliminates the need for monitor and control circuitry.

In another embodiment, the present invention enables LAMP PCR to be performed in a low resource setting. The simple, reusable design permits construction of the device with low-cost raw materials, opening the possibility of point-of-care use for use in water quality assessment, detection of organisms (in food), and assessment of infectious diseases.

In other embodiments, the present invention is comprised of (i) an enclosure that (ii) contains a wax-like substance that has been designed to melt at a predetermined temperature such as 65° C. Blended within the wax is (iii) thermochromic pigment that changes color at the predetermined temperature. The device is heated by (iv) an element powered by rechargeable battery or some other power source. LAMP PCR is performed in wells that hold traditional materials (small microcentrifuge tubes containing the mixture).

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

DETAILED DESCRIPTION OF THE INVENTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

Figure 1:
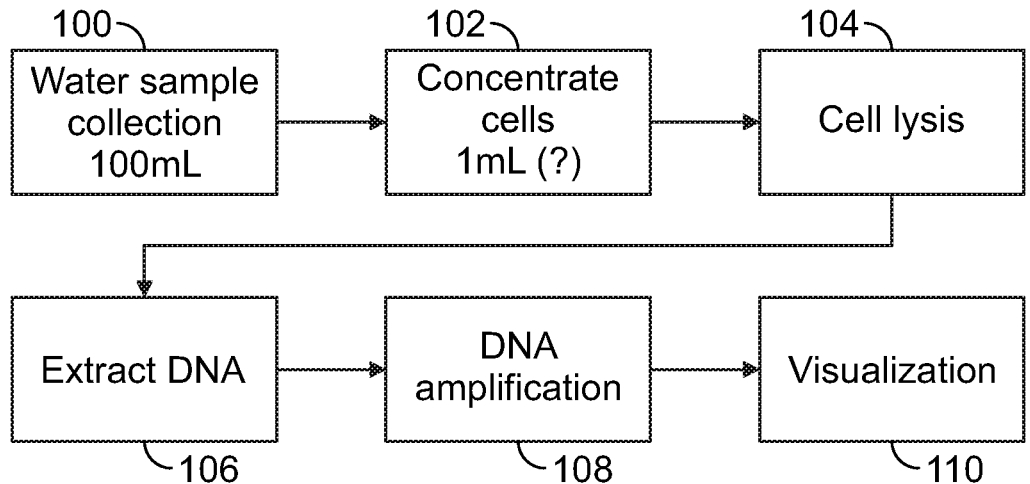
FIG. 1 provides a flowchart for an embodiment of the present invention.

As discussed below, in one embodiment, the present invention provides a system and method enabling LAMP PCR. In a preferred embodiment, as shown in FIG. 1, the present invention may be used to identify an analyte in a solution. For this embodiment, an exemplar of processing a water sample for the detection of DNA is illustrated but the present invention has other applications as well.

As shown in FIG. 1, the present invention provides the steps of collecting a sample (100) which may be a water sample of 100 mL or some other predetermined amount to form a first analyte. The next step is to concentrate the cells (102). Cell lysis is performed (104) to extract DNA (106). DNA amplification (108) is performed next followed by the providing of a visual signal (110) to indicate the presence of an analyte of interest.

Sample collection (100) may be accomplished in any number of known ways including the use of a syringe. In a preferred embodiment sample collection follows the WHO Guideline for Biological Contaminants.

Figure 2:
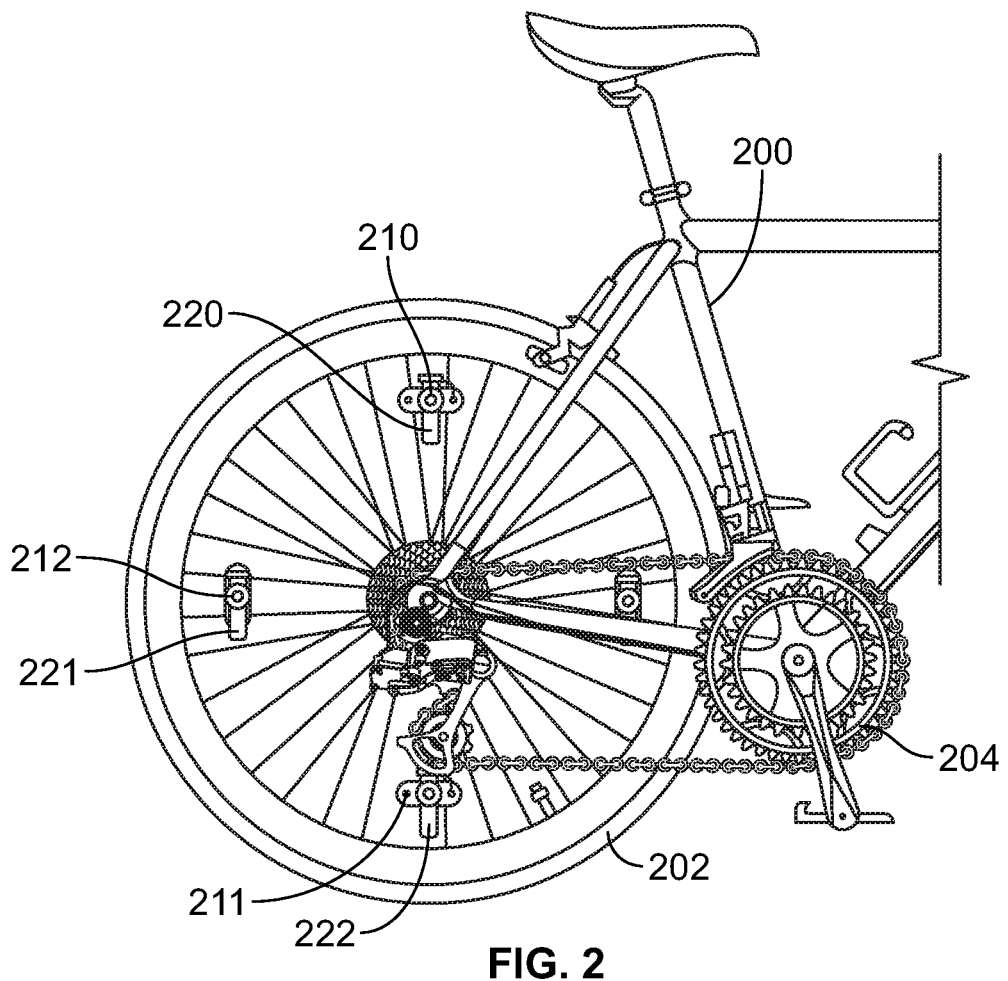
FIG. 2 shows a centrifuge that may be used with an embodiment of the present invention.

Sample concentration (102) may be accomplished in a number of ways known to those of skill in the art. In a preferred embodiment, as shown in FIG. 2, a novel means by which to create a centrifuge is to use bicycle 200 having a wheel 202 connected to a drive mechanism 204. Attached to the spokes of the wheel 202 are one or more adapters 210-212. The adapters, clips or holders that are configured to hold one or more flasks or test tubes 220-222 securely in place while wheel 202 rotates. For a preferred embodiment, to concentrate cells at the bottom of a flask or test tube and to concentrate the solution, which may be water, as a tabulator a velocity of 20 mph on a 26-inch bike tire has been found to produce up to 25 grams of analyte.

Figure 3A:
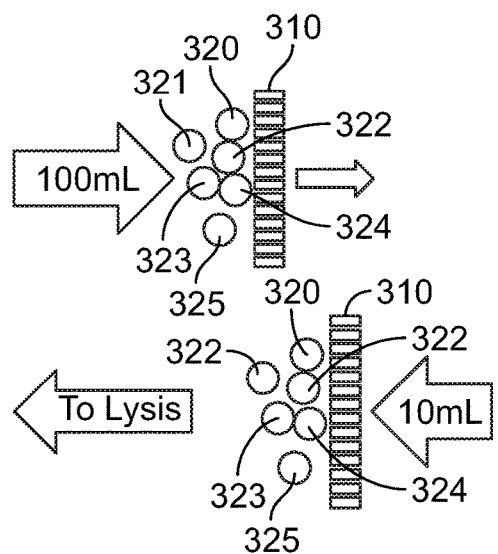
FIGS. 3A-3B illustrate cell washing steps to be performed after sample concentration.
Figure 3B:
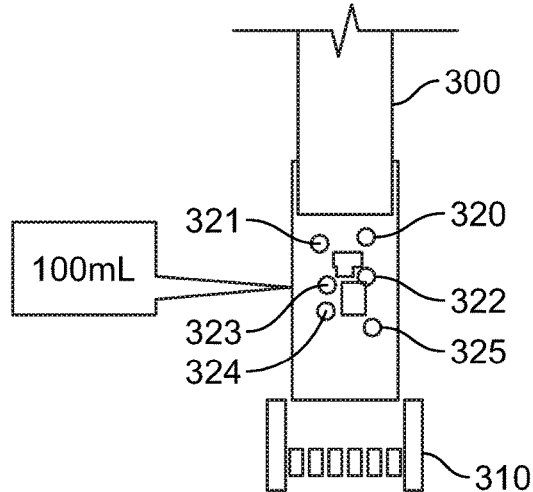

FIGS. 3A-3B illustrate additional steps to be performed after sample concentration (102). As shown in FIGS. 3A and 3B, a primary washing step may be performed. The primary wash may be performed by using a syringe 300 to perform force-fed filtration in combination with membrane 310. As the solution leaves the system, cells 320-325 concentrated on membrane 310. A reverse wash may also be performed but is not necessary. For a reverse wash, approximately 10 mL of pure water or some other solution may be reintroduced into the system so that the cells 320-325 are mixed with the smaller amount of solution to provide a concentrated solution for further processing during lysis.

Figure 4:
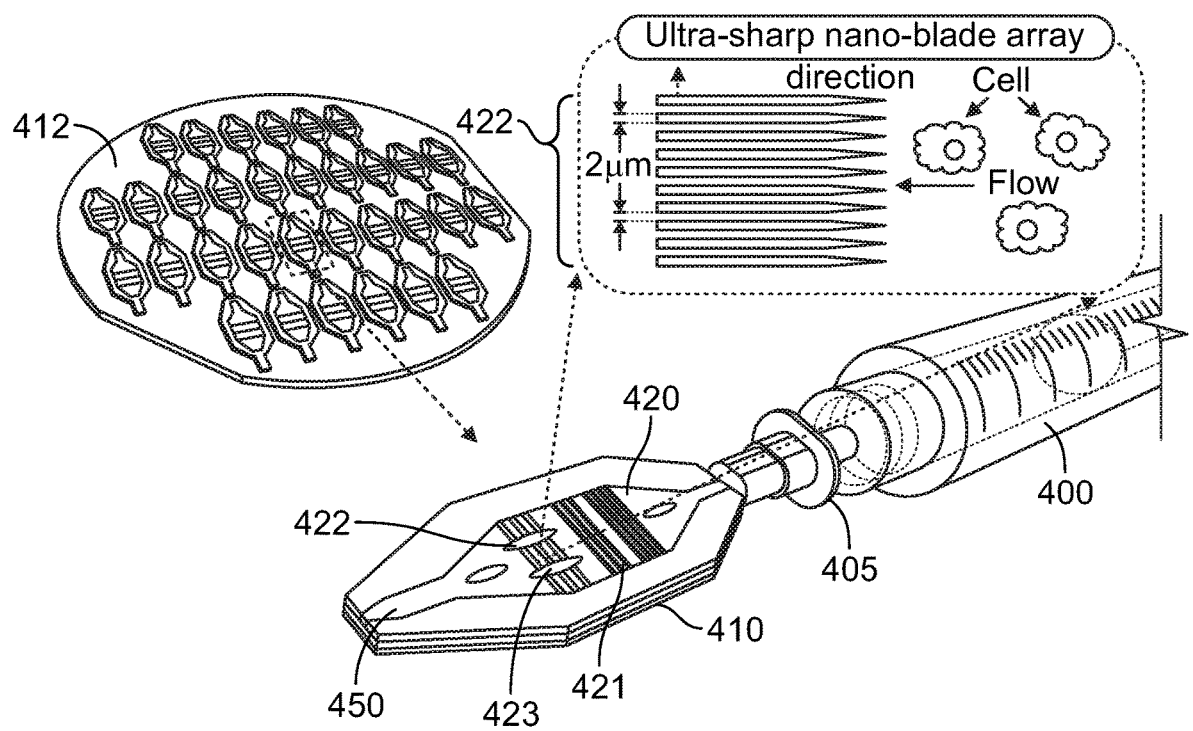
FIG. 4 illustrates an embodiment of the present invention for performing cell lysis.

FIG. 4 illustrates for yet another embodiment of the present invention which provides a means by which to perform lysis (104). In a preferred embodiment, syringe 400 containing a concentrated solution, created as discussed above, is connected by a luer 405, or by some other suitable means, to a disposable mechanical cell lysis chip 410. Chip 410 may be formed on silicon wafer 412 and include a plurality of micro-filter arrays 420 and 421 through which the fluid flows past and towards a plurality of nano blade arrays 422 and 423. While only two blade arrays are designated, as shown in the insert a larger number of blade arrays may be provided.

The blade arrays perform mechanical lysis by shearing the cells as solution is force-fed through the array. The benefits of this include eliminating the need for electricity, chemicals or other mediums. The lysate may then exit the chip through port 450 to form a second analyte for DNA extraction (106).

Figure 5:
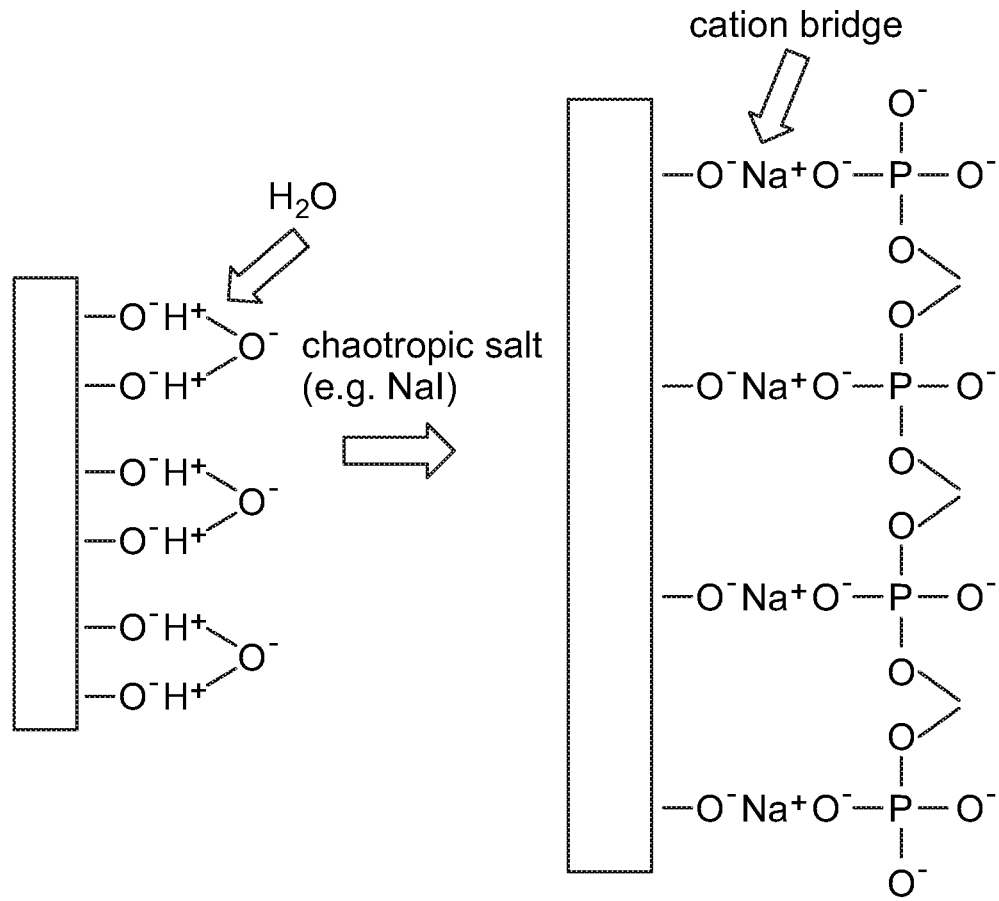
FIG. 5 illustrates DNA extraction by adsorption to silica for an embodiment of the present invention.

As shown in FIG. 5, DNA extraction may be performed by adsorption to silica. In a preferred embodiment, the DNA adsorbed by silica in the presence of chaotropic salt solutions with high ionic strength. A chaotrope denatures biomolecules by disrupting the shell of hydration around them. This allows positively charged ions to form a salt bridge between the negatively charged silica and the negatively charged DNA backbone in chaotropic high salt concentrations. The DNA can then be washed with high salt and ethanol and may then be eluted with a low salt buffer for DNA amplification (108).

Figure 6:
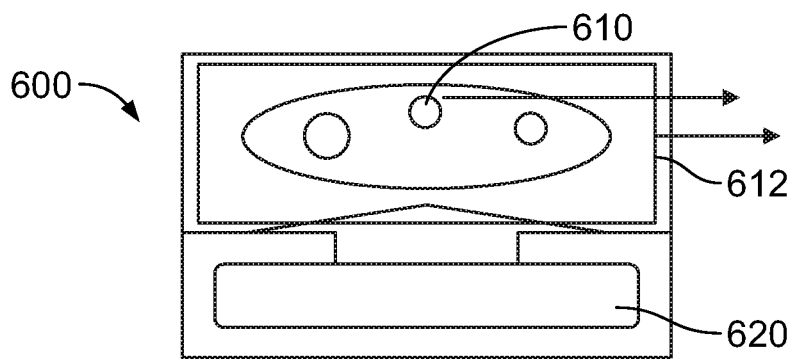
FIG. 6 illustrates an enclosure for visual indication that a predetermined temperature has been reached.

Part of the DNA amplification step includes providing an enclosure or container 600 for elution 610 may contain nucleotides, primers, pathogen DNA, other forms of DNA and other biological materials therein. In a preferred embodiment, as shown in FIG. 6, enclosure 600 includes a phase change material 612. Phase change material 612 may be a wax-like substance that is designed to melt at 65° C. and is blended with a thermochromatic material that changes color at temperature. This provides a visual detection that the heating has been completed. Heater 620 is also provided. Heater 620 may be chemical or use a filament used in combination with an energy source such as a rechargeable or disposable battery.

Once the solution has been properly heated DNA visualization (110) may be performed. In a preferred embodiment visualization is performed by staining any potential DNA in the solution with a dye. In a preferred embodiment, dyeing may be performed using the SYBR green technique that is known to those of skill in the art. For this technique, SYBR green dye his positively charged and binds to DNA. The dye absorbs blue light and emits green light to indicate the presence of DNA.

In yet other embodiments, the present invention provides a method and system testing a material for the presence of DNA without the use of an electric current. The system and method include the steps of obtaining a sample of solution of cells to form a first analyte; concentrating the cells in a first analyte, which may be done with a mechanical centrifuge such as a bicycle wheel; lysing the cells which may be done use of the microchip; extracting DNA from the cells to form a second analyte. The second analyte is chemically heated in an enclosure that contains a material that melts at a predetermined temperature and includes a thermochromic pigment that changes color at a temperature equal to or greater than the predetermined temperature.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above-described embodiments, methods, and examples, but by all embodiments and methods within the scope and spirit of the disclosure.

What is claimed is:

1. A method for testing a material comprising the steps of:
obtaining a sample of solution of cells forming a first analyte and placing said sample in an enclosure;
concentrating said cells in said first analyte;
lysing said cells;
extracting DNA from said cells to form a second analyte;
applying heat at predetermined temperature to said enclosure to amplify said DNA in said second analyte;
using a phase change material that melts at a predetermined temperature to maintain said predetermined temperature during said heating; and
detecting said DNA.

2. The method of claim 1 wherein said material is a wax that includes a thermochromic pigment that changes color at temperature.

3. The method of claim 1 further including a heating element.

4. The method of claim 3 wherein the heating element is powered by a battery.

5. The method of claim 3 wherein the heating element is powered by a rechargeable battery.

6. The method of claim 1 wherein said cells are concentrated in said first analyte by locating said first analyte in one or more containers, affixing said one or more containers to a bicycle wheel, and spinning said wheel.

7. The method of claim 1 further including the step of heating said second analyte by chemical heating.

8. The method of claim 1 wherein said visualization is performed by staining DNA in said second analyte with a dye.

9. The method of claim 8 wherein said dyeing is performed using an SYBR green technique.

10. The method of claim 1 wherein DNA extraction is performed by adsorption to silica.

11. The method of claim 10 wherein DNA adsorbed by silica in the presence of chaotropic salt solutions.

12. A method for testing a material for the presence of DNA without the use of an electric current comprising the steps of:
obtaining a sample of solution of cells to form a first analyte;
concentrating said cells in said first analyte;
lysing said cells;
extracting DNA from said cells to form a second analyte, said second analyte is heated at a predetermined temperture in an enclosure lined with a phase change material that melts at a predetermined temperature to maintain said predetermined temperature during heating and includes a thermochromic pigment that changes color at a temperature equal to or greater than said predetermined temperature;
detecting said DNA.

13. The method of claim 12 wherein said cells are concentrated in said first analyte by locating said first analyte in one or more containers, affixing said one or more containers to a bicycle wheel, and spinning said wheel.

14. The method of claim 12 further including the step of heating said second analyte by chemical heating.

15. The method of claim 12 wherein said visualization is performed by staining DNA in said second analyte with a dye.

16. The method of claim 15 wherein said dyeing is performed using an SYBR green technique.

17. The method of claim 12 wherein DNA extraction is performed by adsorption to silica.

18. The method of claim 12 wherein DNA adsorbed by silica in the presence of chaotropic salt solutions.

19. The method of claim 12, wherein said DNA in said second analyte are enclosed by said phase change material.

20. The method of claim 1 wherein said enclosure is lined with said phase change material.

* * * * *